US008257979B2

(12) United States Patent
Balogh et al.

(10) Patent No.: US 8,257,979 B2
(45) Date of Patent: Sep. 4, 2012

(54) METHOD FOR CHARACTERIZING THE POROSITY IN FUEL CELL ELECTRODES

(75) Inventors: Michael P. Balogh, Novi, MI (US); Frederick A. Hayes, Dixon, CA (US)

(73) Assignee: GM Global Technology Operations LLC, Detroit, MI (US)

( * ) Notice: Subject to any disclaimer, the term of this patent is extended or adjusted under 35 U.S.C. 154(b) by 845 days.

(21) Appl. No.: 11/938,521

(22) Filed: Nov. 12, 2007

(65) Prior Publication Data
US 2009/0124020 A1    May 14, 2009

(51) Int. Cl.
G01N 27/00    (2006.01)
(52) U.S. Cl. ............................. 436/164; 521/27; 429/90
(58) Field of Classification Search ........................ None
See application file for complete search history.

(56) References Cited

U.S. PATENT DOCUMENTS

2007/0093561 A1*   4/2007   Yu et al. ........................... 521/27
2008/0075999 A1*   3/2008   Izuhara et al. ................... 429/33

OTHER PUBLICATIONS

Cheever, Gordon D., et al. Adsorption of Some Organic Surfactants on Rutile Surfaces, 1964, Electron Microscope Studies, vol. 3(2), pp. 89-94.*
Sarada, T., Sawyer, L.C. and Ostler, M.I., "Three Dimensional Structure of Celgard Microporous Membranes", Journal of Membrane Science, 15 (1983) 97-113, Elsevier Science Publishers, R V Amsterdam—Printed in the Netherlands.

* cited by examiner

*Primary Examiner* — Yelena G Gakh
*Assistant Examiner* — Robert Xu
(74) *Attorney, Agent, or Firm* — John A. Miller; Miller IP Group, PLC

(57) ABSTRACT

A method for evaluating the composition of an MEA for a fuel cell. The method includes soaking the MEA in an unsaturated organic compound for a predetermined period of time, and then allowing the MEA to dry. The method then includes staining the MEA with osmium tetroxide ($OsO_4$) in a closed container. The stained MEA is then encased in an epoxy. Thin sections of the encapsulated MEA are then prepared, and the sections are viewed through a transmission electron microscope. The stained MEA will show dark regions where the ionomer and carbon particles are located and lighter regions that are epoxy filled pores.

15 Claims, 3 Drawing Sheets

METHOD FOR CHARACTERIZING THE POROSITY IN FUEL CELL ELECTRODES

BACKGROUND OF THE INVENTION

1. Field of the Invention

This invention relates generally to a method for evaluating the porosity of a membrane electrode assembly (MEA) and, more particularly, to a method for evaluating the porosity of a fuel cell MEA including treating the MEA with an unsaturated organic compound and then staining the MEA with osmium tetroxide to provide a visual differentiation between the particles in the MEA and the pores therebetween.

2. Discussion of the Related Art

Hydrogen is a very attractive fuel because it is clean and can be used to efficiently produce electricity in a fuel cell. A hydrogen fuel cell is an electro-chemical device that includes an anode and a cathode with an electrolyte therebetween. The anode receives hydrogen gas and the cathode receives oxygen or air. The hydrogen gas is dissociated in the anode to generate free hydrogen protons and electrons. The hydrogen protons pass through the electrolyte to the cathode. The hydrogen protons react with the oxygen and the electrons in the cathode to generate water. The electrons from the anode cannot pass through the electrolyte, and thus are directed through a load to perform work before being sent to the cathode.

Proton exchange membrane fuel cells (PEMFC) are a popular fuel cell for vehicles. The PEMFC generally includes a solid polymer electrolyte proton conducting membrane, such as a perfluorosulfonic acid membrane. The anode and cathode typically include finely divided catalytic particles, usually platinum (Pt), supported on carbon particles and mixed with an ionomer. The catalytic mixture is deposited on opposing sides of the membrane. The combination of the anode catalytic mixture, the cathode catalytic mixture and the membrane define a membrane electrode assembly (MEA). MEAs are relatively expensive to manufacture and require certain conditions for effective operation.

Several fuel cells are typically combined in a fuel cell stack to generate the desired power. For example, a typical fuel cell stack for a vehicle may have two hundred or more stacked fuel cells. The fuel cell stack receives a cathode input gas, typically a flow of air forced through the stack by a compressor. Not all of the oxygen is consumed by the stack and some of the air is output as a cathode exhaust gas that may include water as a stack by-product. The fuel cell stack also receives an anode hydrogen input gas that flows into the anode side of the stack.

The fuel cell stack includes a series of bipolar plates positioned between the several MEAs in the stack, where the bipolar plates and the MEAs are positioned between two end plates. The bipolar plates include an anode side and a cathode side for adjacent fuel cells in the stack. Anode gas flow channels are provided on the anode side of the bipolar plates that allow the anode reactant gas to flow to the respective MEA. Cathode gas flow channels are provided on the cathode side of the bipolar plates that allow the cathode reactant gas to flow to the respective MEA. One end plate includes anode gas flow channels, and the other end plate includes cathode gas flow channels. The bipolar plates and end plates are made of a conductive material, such as stainless steel or a conductive composite. The end plates conduct the electricity generated by the fuel cells out of the stack. The bipolar plates also include flow channels through which a cooling fluid flows.

It is known in the MEA art to coat the catalyst layer on the polymer electrolyte membrane. The catalyst layer may be deposited directly on the membrane, or indirectly applied to the membrane by first coating the catalyst on a decal substrate. Typically the catalyst is coated on the decal substrate as a slurry by a rolling process. The catalyst is then transferred to the membrane by a hot-pressing step. This type of MEA fabrication process is sometimes referred to as a catalyst coated membrane (CCM).

After the catalyst is coated on the decal substrate, an ionomer layer is sometimes sprayed over the catalyst layer before it is transferred to the membrane. Because both the catalyst and the membrane include the ionomer, the ionomer spray layer provides a better contact between the catalyst and the membrane, because it decreases the contact resistance between the catalyst and the membrane. This increases the proton exchange between the membrane and the catalyst, and thus, increases fuel cell performance.

The decal substrate can be a porous expanded polytetrafluoroethylene (ePTFE) decal substrate. However, the ePTFE substrate is expensive and not reusable. Particularly, when the catalyst is transferred to the membrane on the ePTFE substrate, a certain portion of the catalyst or catalyst components remain on the ePTFE substrate. Additionally, the ePTFE substrate stretches, deforms and absorbs solvents making a cleaning step very difficult. Hence, every ePTFE substrate used to make each anode and cathode is discarded.

The decal substrate can also be a non-porous ethylene tetrafluoroethylene (ETFE) decal substrate. The ETFE decal substrate provides minimal loss of catalyst and ionomer to the substrate because virtually all of the coating is decal transferred. The substrate does not deform and can be reused. For both of these processes, the anode and cathode decal substrates are cut to the dimensions of the final electrode size, then hot-pressed to the perfluorinated membrane, and subsequently, the decal substrate is pealed off.

As discussed above, the MEA includes a mixture of platinum supported on carbon particles that is mixed with an ionomer. The ionomer has a tendency to encapsulate the carbon particles, sometimes covering the platinum particles. In order to optimize the performance of the MEA, it is necessary to optimize the mixture that makes up the MEA. Thus, it is necessary to differentiate the various materials in the MEA, such as the size of the carbon particles, the distribution of the platinum particles, the amount of the ionomer, the size and shape of the pores between the various materials, etc. Further, it is desirable to minimize the amount of platinum in the MEA because of its expense. However, because the different materials include some of the same components, such as carbon, it is difficult to differentiate them when looking through a microscope. There currently is no suitable technique for differentiating the various materials in an MEA.

SUMMARY OF THE INVENTION

In accordance with the teachings of the present invention, a method is disclosed for evaluating the composition of an MEA for a fuel cell. The method includes soaking the MEA in an unsaturated organic compound for a predetermined period of time, and then allowing the MEA to dry. The method then includes staining the MEA with osmium tetroxide ($OsO_4$) in a closed container. The stained MEA is then encapsulated in an epoxy. Thin sections of the encapsulated MEA are then prepared, and the thin sections are viewed through a transmission electron microscope. The stained MEA will show dark regions where the ionomer and carbon particles are located and lighter regions that are epoxy filled pores.

Additional features of the present invention will become apparent from the following description and appended claims, taken in conjunction with the accompanying drawings.

DETAILED DESCRIPTION OF THE EMBODIMENTS

The following discussion of the embodiments of the invention directed to a method for treating an MEA so that the composition of the MEA can be visually identified is merely exemplary in nature, and is in no way intended to limit the invention or its applications or uses.

Figure 1:
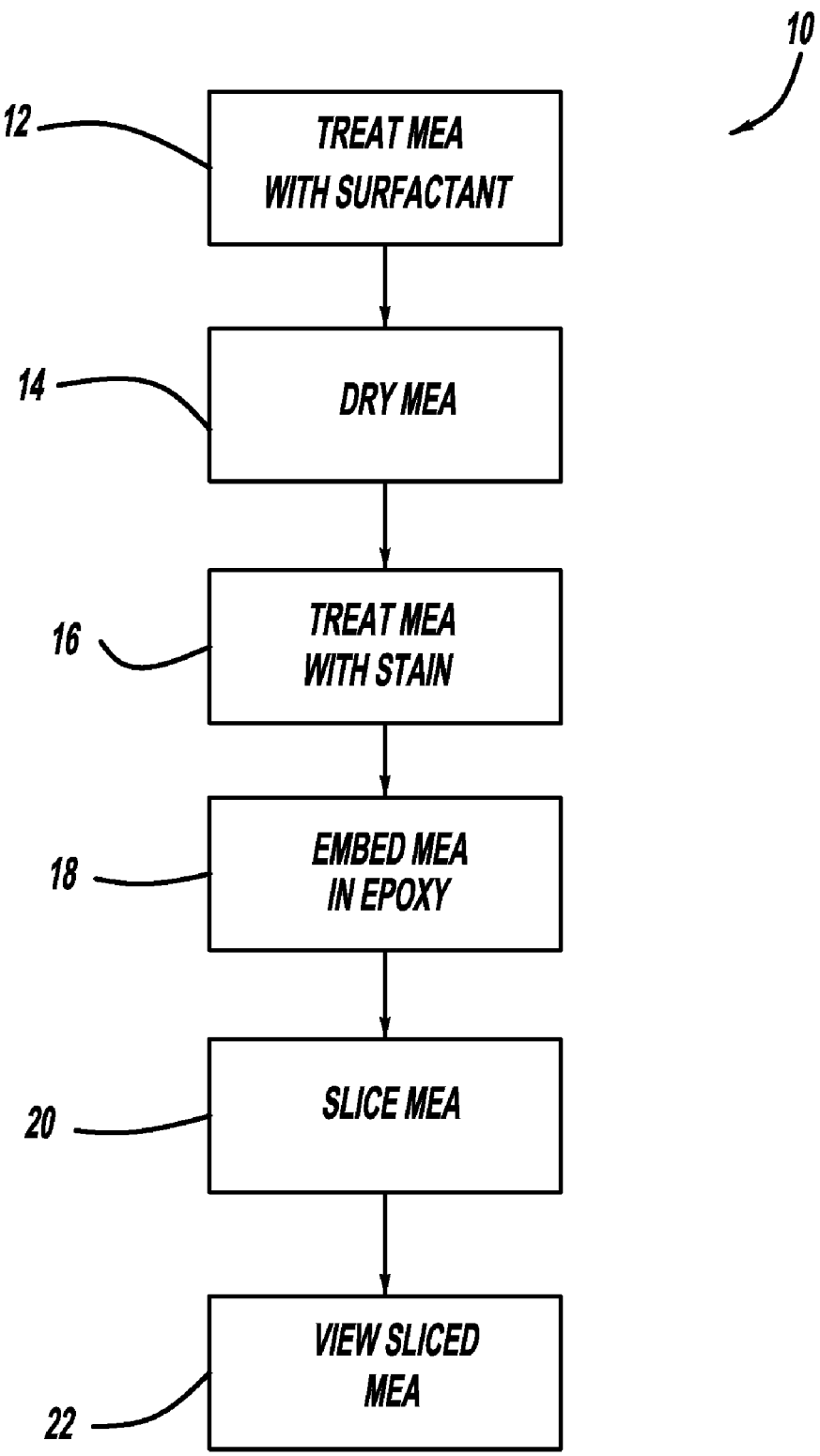
FIG. 1 is a flow chart diagram showing a process for treating an MEA so that the composition of the MEA can be evaluated, according to an embodiment of the present invention.

FIG. 1 is a flow chart diagram 10 showing a method for evaluating the composition of the electrodes of an MEA for a fuel cell, according to an embodiment of the present invention. The process includes soaking a piece of the MEA in an unsaturated organic compound at box 12. Any suitable unsaturated organic compound that reacts with carbon and/or a heavy metal can be used for the purposes described herein, such as a 0.5-2 wt % solution of Brij 97 (polyoxyethylene 10 oleyl ether). Further, the piece of the MEA can be soaked in the unsaturated organic compound for any suitable period of time to completely saturate the MEA, for example, up to one hour. The unsaturated organic compound is absorbed by the ionomer in the MEA. The piece of the MEA is then removed from the unsaturated organic compound solution, rinsed and dried at box 14.

The MEA is then treated with a suitable stain. In one embodiment, the stain is an oxidizing stain, such as osmium tetroxide ($OsO_4$), where the reaction between the osmium tetroxide causes the unsaturated organic compound to be stained or darkened. Because osmium tetroxide is such a large oxidizing agent and is a gas, it is necessary to take precautions when using osmium tetroxide. In one embodiment, the osmium tetroxide is reacted with the MEA in a closed container at 50° C. for 15-20 hours. When the osmium tetroxide gas reacts with the unsaturated organic compound, the osmium tetroxide gas turns into a solid that is very opaque.

The stained piece of MEA is then embedded in an epoxy at box 18. Because the pores in the MEA do not include the an unsaturated organic compound, they are not stained by the osmium tetroxide. However, before the MEA can be viewed, the holes have to be filled with a clear substance so that the three dimension structure of the MEA can be viewed without the pores collapsing. In one embodiment, the piece of the MEA is placed in a vacuum container, the gas is pumped out of the container, and the epoxy is dripped onto the MEA. When the pressure is reintroduced into the container, the epoxy is forced into the pores of the MEA. After the epoxy has cured, the MEA is then sliced to provide thin sections of the MEA at box 20. In one embodiment, a microtome machine is used to slice the sections of the MEA.

The thin sections of the MEA are then mounted in a suitable viewing machine, such as a transmission electron microscope (TEM). The TEM produces micrograph images of the sliced MEA.

Figure 2:
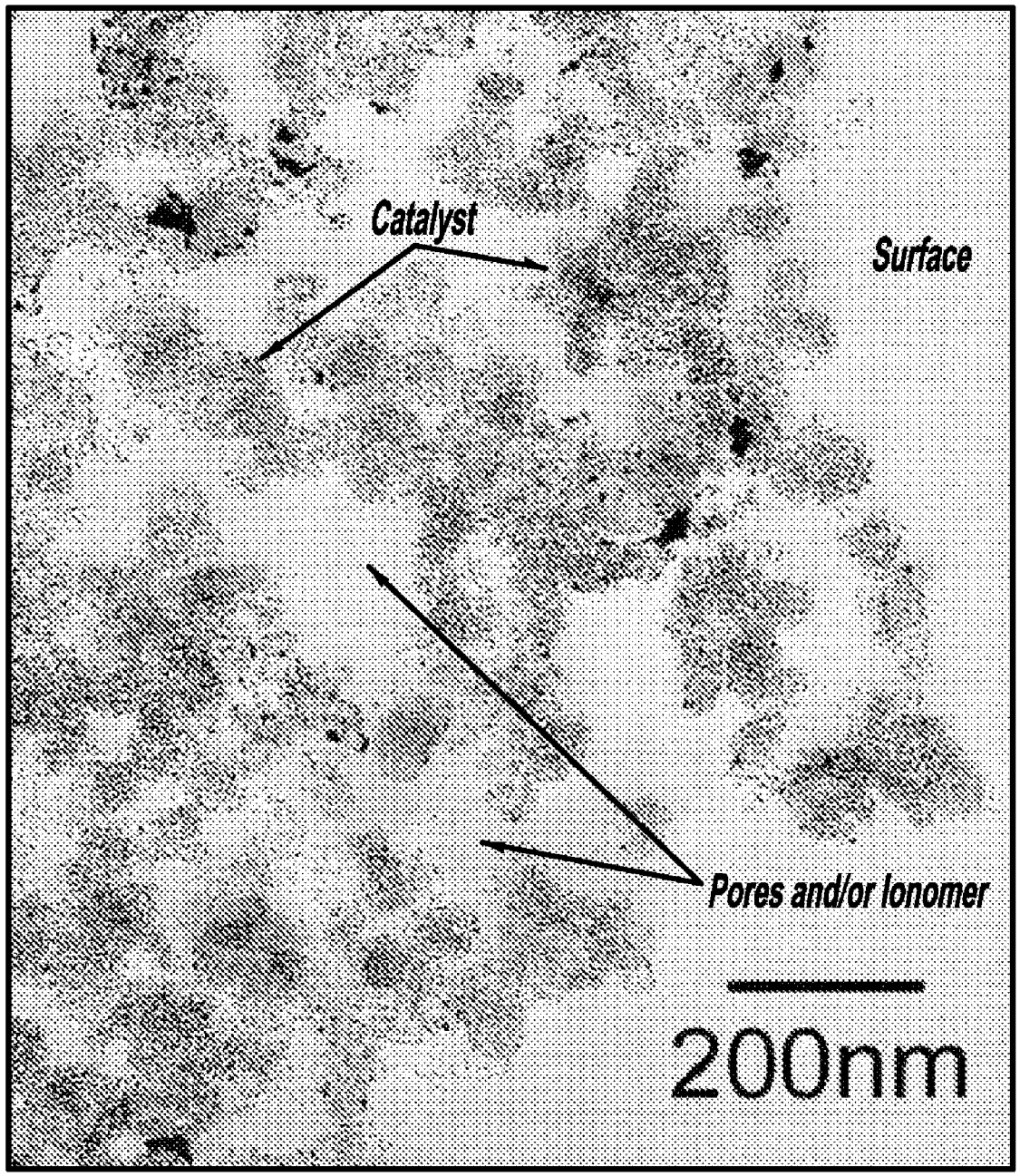
FIG. 2 is a magnified TEM micrograph of a portion of an MEA that has not been stained.

The stained piece of MEA provides the contrast to visually differentiate the structure of the MEA from the pores. FIG. 2 is a magnified TEM micrograph that has not been treated by the staining process of the invention. The catalyst is identified as the darker regions and the pores and ionomer are identified as the lighter regions. Thus, the pores and the ionomer are not distinguishable from each other, making an evaluation of the composition of the MEA impossible.

Figure 3:
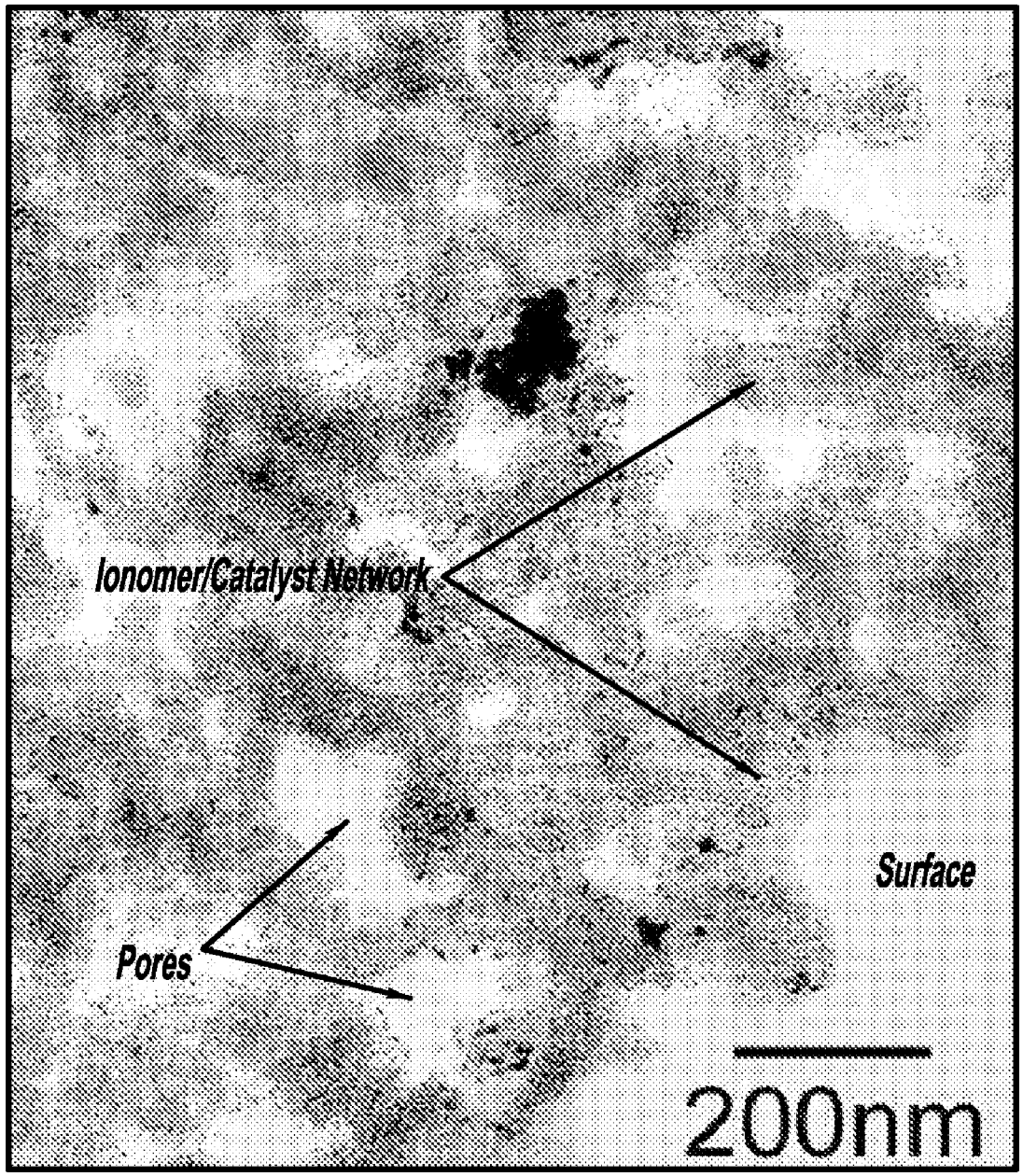
FIG. 3 is a magnified TEM micrograph of a portion of an MEA that has been stained according to the process of the invention.

FIG. 3 is a TEM micrograph at the same magnification that has been treated by the staining process of the invention. In this micrograph, the staining process has darkened both the ionomer and the catalyst, and the epoxy filled pores remain lighter. Therefore, it is readily straightforward to evaluate the pores of the MEA. Thus, the staining process provides a suitable contrast between the pores and the ionomer so that the MEA can be characterized and evaluated. The size of the pores can be evaluated and the volume of the pores can be determined.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. A method for evaluating the composition of a membrane electrode assembly (MEA) to differentiate elements in the MEA, said method comprising:
   treating the MEA with an unsaturated organic compound;
   treating the MEA with a staining material that reacts with the unsaturated organic compound and causes it to be darkened;
   filling pores in the MEA with a light material; and
   viewing the MEA so as to differentiate the lighter filled pores from the darker stained areas of the MEA.

2. The method according to claim 1 wherein treating the MEA with an unsaturated organic compound includes treating the MEA with an unsaturated organic compound that reacts with carbon.

3. The method according to claim 1 wherein treating the MEA with an unsaturated organic compound includes treating the MEA with a polyoxyethylene 10 oleyl ether.

4. The method according to claim 3 wherein the unsaturated organic compound is a 0.5-2 wt % an unsaturated organic compound in a solution of water.

5. The method according to claim 1 wherein treating the MEA with an unsaturated organic compound includes treating the MEA with an unsaturated organic compound that attaches to an ionomer.

6. The method according to claim 1 wherein treating the MEA with a staining material includes treating the MEA with an oxidizing agent that reacts within an unsaturated organic compound.

7. The method according to claim 5 wherein treating the MEA with a staining material includes treating the MEA with osmium tetroxide.

8. The method according to claim 1 wherein filling pores in the MEA includes embedding the MEA in an epoxy.

9. The method according to claim 1 wherein viewing the MEA includes using a transmission electron microscope.

10. The method according to claim 1 further comprising slicing the MEA before it is viewed.

11. The method according to claim 1 wherein the MEA is a fuel cell MEA.

12. A method for evaluating the composition of a membrane electrode assembly (MEA) to differentiate elements in the MEA, said method comprising:

treating the MEA with an unsaturated organic compound that reacts with carbon;

treating the MEA with osmium tetroxide that reacts with the unsaturated organic compound and causes it to be darkened;

filling pores in the MEA with an epoxy;

slicing the MEA into thin sections; and viewing images of the MEA slices using a transmission electron microscope so as to differentiate the epoxy filled pores from the darker stained areas of the MEA.

13. The method according to claim 12 wherein treating the MEA with an unsaturated organic compound includes treating the MEA with polyoxyethylene 10 oleyl ether.

14. The method according to claim 13 wherein the unsaturated organic compound is a 0.5-2 wt % an unsaturated organic compound in a solution of water.

15. The method according to claim 12 wherein the MEA is a fuel cell MEA.

\* \* \* \* \*